(12) United States Patent
Beulke et al.

(10) Patent No.: US 7,875,051 B2
(45) Date of Patent: Jan. 25, 2011

(54) EMBOLIC PROTECTION FILTER HAVING AN IMPROVED FILTER FRAME

(75) Inventors: Mel R. Beulke, Bloomington, MN (US); Horng-Ban Lin, Maple Grove, MN (US); Gary R. Kostur, Golden Valley, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1119 days.

(21) Appl. No.: 11/556,017

(22) Filed: Nov. 2, 2006

(65) Prior Publication Data

US 2007/0060947 A1 Mar. 15, 2007

Related U.S. Application Data

(63) Continuation of application No. 10/352,409, filed on Jan. 28, 2003, now abandoned.

(51) Int. Cl.
*A61M 29/00* (2006.01)

(52) U.S. Cl. ...................................... 606/200

(58) Field of Classification Search ................ 606/159, 606/194, 198, 200, 167; 604/22, 96
See application file for complete search history.

(56) References Cited

U.S. PATENT DOCUMENTS

| | | | |
|---|---|---|---|
| 3,472,230 A | 10/1969 | Forgarty |
| 3,952,747 A | 4/1976 | Kimmell, Jr. |
| 3,996,938 A | 12/1976 | Clark, III |
| 4,425,908 A | 1/1984 | Simon |
| 4,643,184 A | 2/1987 | Mobin-Uddin |
| 4,662,885 A | 5/1987 | DiPisa, Jr. |
| 4,706,671 A | 11/1987 | Weinrib |
| 4,723,549 A | 2/1988 | Wholey et al. |
| 4,790,812 A | 12/1988 | Hawkins, Jr. et al. |
| 4,790,813 A | 12/1988 | Kensey |
| 4,794,928 A | 1/1989 | Kletschka |
| 4,857,045 A | 8/1989 | Rydell |
| 4,873,978 A | 10/1989 | Ginsburg |
| 4,886,061 A | 12/1989 | Fischell et al. |
| 4,969,891 A | 11/1990 | Gewertz |
| 5,011,488 A | 4/1991 | Ginsburg |
| 5,071,407 A | 12/1991 | Termin et al. |
| 5,133,733 A | 7/1992 | Rasmussen et al. |
| 5,160,342 A | 11/1992 | Reger et al. |
| 5,192,286 A | 3/1993 | Phan et al. |
| 5,324,304 A | 6/1994 | Rasmussen |
| 5,329,942 A | 7/1994 | Gunther et al. |
| 5,370,657 A | 12/1994 | Irie |
| 5,415,630 A | 5/1995 | Gory et al. |
| 5,419,774 A | 5/1995 | Willard et al. |
| 5,462,529 A | 10/1995 | Simpson et al. |

(Continued)

FOREIGN PATENT DOCUMENTS

WO 96/01591 A1 1/1996

*Primary Examiner*—Michael J Milano
*Assistant Examiner*—Victor X Nguyen
(74) *Attorney, Agent, or Firm*—Seager, Tufte & Wickhem, LLC

(57) ABSTRACT

An embolic protection filter having an improved filter frame and method of making the same. In at least some embodiments, the present invention includes an embolic protection filter coupled to an elongate shaft. The filter may include a filter frame assembly having one or more frame members. The frame members may include a filter mouth defining portion.

19 Claims, 11 Drawing Sheets

U.S. PATENT DOCUMENTS

| | | | |
|---|---|---|---|
| 5,536,242 | A | 7/1996 | Willard et al. |
| 5,549,626 | A | 8/1996 | Miller et al. |
| 5,662,671 | A | 9/1997 | Barbut et al. |
| 5,669,933 | A | 9/1997 | Simon et al. |
| 5,769,816 | A | 6/1998 | Barbut et al. |
| 5,779,716 | A | 7/1998 | Cano et al. |
| 5,800,457 | A | 9/1998 | Gelbfish |
| 5,800,525 | A | 9/1998 | Bachinski et al. |
| 5,807,398 | A | 9/1998 | Shaknovich |
| 5,814,064 | A | 9/1998 | Daniel et al. |
| 5,833,650 | A | 11/1998 | Imran |
| 5,848,964 | A | 12/1998 | Samuels |
| 5,911,734 | A | 6/1999 | Tsugita et al. |
| 6,066,149 | A | 5/2000 | Samson et al. |
| 6,066,158 | A | 5/2000 | Engelson et al. |
| 6,142,987 | A | 11/2000 | Tsugita |
| 6,152,946 | A | 11/2000 | Broome et al. |
| 6,168,579 | B1 | 1/2001 | Tsugita |
| 6,171,327 | B1 | 1/2001 | Daniel et al. |
| 6,179,861 | B1 | 1/2001 | Khosravi et al. |
| 6,203,561 | B1 | 3/2001 | Ramee et al. |
| 6,206,868 | B1 | 3/2001 | Parodi |
| 6,221,006 | B1 | 4/2001 | Dubrul et al. |
| 6,277,139 | B1 | 8/2001 | Levinson et al. |
| 6,530,939 | B1 | 3/2003 | Hopkins et al. |
| 6,544,279 | B1 | 4/2003 | Hopkins et al. |
| 6,589,263 | B1 * | 7/2003 | Hopkins et al. .............. 606/200 |
| 6,605,102 | B1 | 8/2003 | Mazzocchi et al. |
| 6,610,077 | B1 | 8/2003 | Hancock et al. |
| 6,702,834 | B1 | 3/2004 | Boylan et al. |
| 6,939,361 | B1 * | 9/2005 | Kleshinski ................... 606/200 |
| 2002/0183783 | A1 | 12/2002 | Shadduck |
| 2002/0188314 | A1 | 12/2002 | Anderson et al. |
| 2003/0065355 | A1 * | 4/2003 | Weber ........................ 606/200 |
| 2003/0149475 | A1 | 8/2003 | Hyodoh et al. |
| 2004/0093012 | A1 | 5/2004 | Cully et al. |
| 2004/0199201 | A1 | 10/2004 | Kellett et al. |
| 2005/0101989 | A1 | 5/2005 | Cully et al. |
| 2005/0177186 | A1 | 8/2005 | Cully et al. |

* cited by examiner

EMBOLIC PROTECTION FILTER HAVING AN IMPROVED FILTER FRAME This application is a continuation of U.S. application Ser. No. 10/352,409 filed Jan. 28, 2003.

FIELD OF THE INVENTION

The present invention pertains to embolic protection devices. More particularly, the present invention pertains to embolic protection devices having a refined filter frame.

BACKGROUND

Heart and vascular disease are majors problem in the United States and throughout the world. Conditions such as atherosclerosis result in blood vessels becoming blocked or narrowed. This blockage can result in lack of oxygenation of the heart, which has significant consequences since the heart muscle must be well oxygenated in order to maintain its blood pumping action.

Occluded, stenotic, or narrowed blood vessels may be treated with a number of relatively non-invasive medical procedures including percutaneous transluminal angioplasty (PTA), percutaneous transluminal coronary angioplasty (PTCA), and atherectomy. Angioplasty techniques typically involve the use of a balloon catheter. The balloon catheter is advanced over a guidewire such that the balloon is positioned adjacent a stenotic lesion. The balloon is then inflated and the restriction of the vessel is opened. During an atherectomy procedure, the stenotic lesion may be mechanically cut away from the blood vessel wall using an atherectomy catheter.

During angioplasty and atherectomy procedures, embolic debris can be separated from the wall of the blood vessel. If this debris enters the circulatory system, it could block other vascular regions including the neural and pulmonary vasculature. During angioplasty procedures, stenotic debris may also break loose due to manipulation of the blood vessel. Because of this debris, a number of devices, termed embolic protection devices, have been developed to filter out this debris.

BRIEF SUMMARY

The present invention pertains to refinements to embolic protection filters, frames, and methods of making the same. In some embodiments, an embolic protection filter device includes an elongate shaft having an embolic protection filter coupled thereto. The filter may include a filter frame assembly and a filter material or fabric coupled to the filter assembly.

In at least some embodiments, the filter frame assembly may include two or more filter member. Each filter member may include a filter mouth defining portion and a shaft engaging portion. Including a plurality of filter members may incorporate a number of desirable features into the filtering device as described in more detail below.

DETAILED DESCRIPTION

Figure 1:
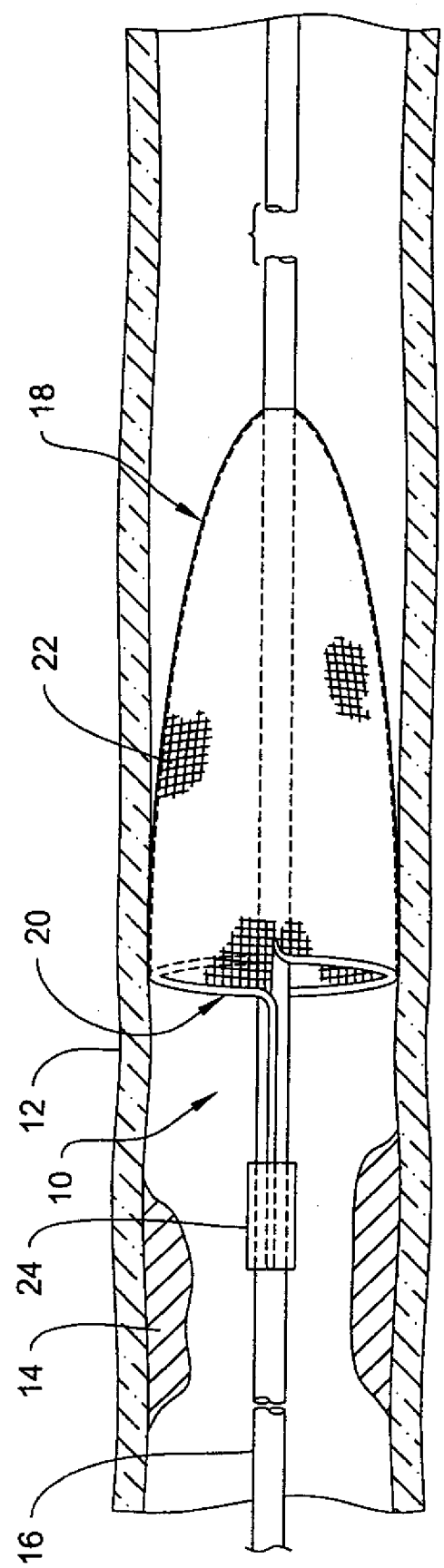
FIG. 1 is a partial cross-sectional view of an example embolic protection device disposed within a body lumen.

The following description should be read with reference to the drawings wherein like reference numerals indicate like elements throughout the several views. The detailed description and drawings illustrate example embodiments of the claimed invention.

FIG. 1 is a partial cross-sectional view of an example embolic protection device 10 disposed within a blood vessel 12 adjacent an intravascular lesion 14. In at least some embodiments, device 10 can be used to filter embolic debris generated, for example, by treatment of lesion 14. Device 10 may include an elongate shaft or guidewire 16 having an embolic protection filter 18 coupled thereto. Device 10 may include a number of refinements that, for example, improve apposition of the walls of blood vessel 12 by filter 18, shorten the landing zone of filter 18, shorten the vessel footprint, as well as other desirable features as described in more detail below.

Filter 18 may include a filter frame assembly 20 and a filter material or fabric 22 coupled to frame assembly 20. In general, filter 18 may be adapted to operate between a first generally collapsed configuration and a second generally expanded configuration for collecting debris in a body lumen. Filter material 22 can be drilled (for example, formed by known laser techniques) or otherwise manufactured to include at least one opening. The holes or openings can be sized to allow blood flow therethrough but restrict flow of debris or emboli floating in the body lumen or cavity. Frame assembly 20 may be coupled to shaft 16 by a coupling 24. Coupling 24 may be one or more windings of frame assembly about shaft 16 or may be a fitting disposed over an end of frame assembly 20 to attach it to shaft 16.

Figure 2:
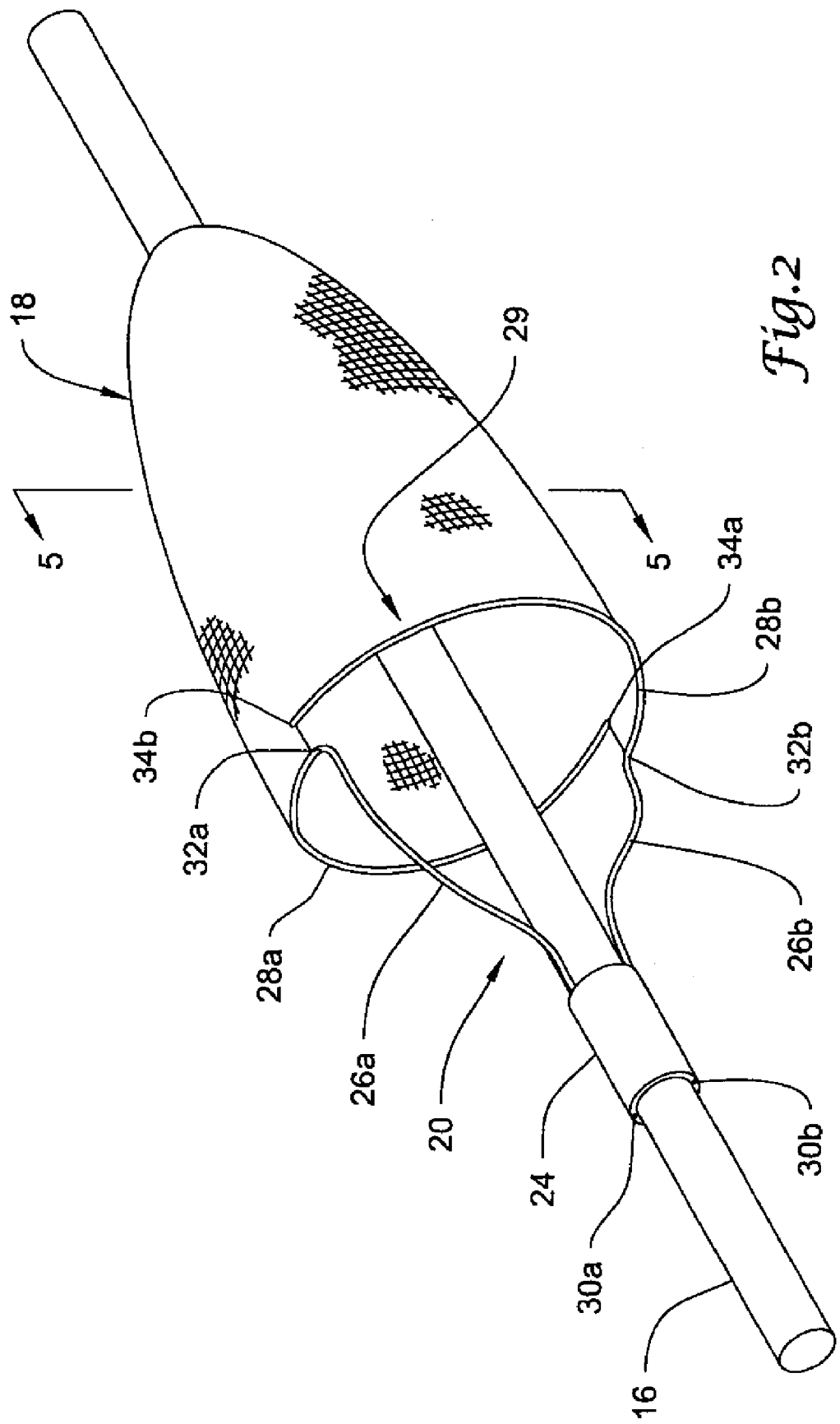
FIG. 2 is a perspective view of an example embolic protection device.

Frame assembly 20 may include one or more frame members 26. For example, a perspective view of an example frame assembly 20 having two frame members, indicated by reference numbers 26a and 26b, is shown in FIG. 2. It can be appreciated, however, that the precise number of frame members 26 can be altered without departing from the spirit of the invention. For example, it may be desirable to include three or more frame members 26 in alternative example frame assemblies.

Figure 3:
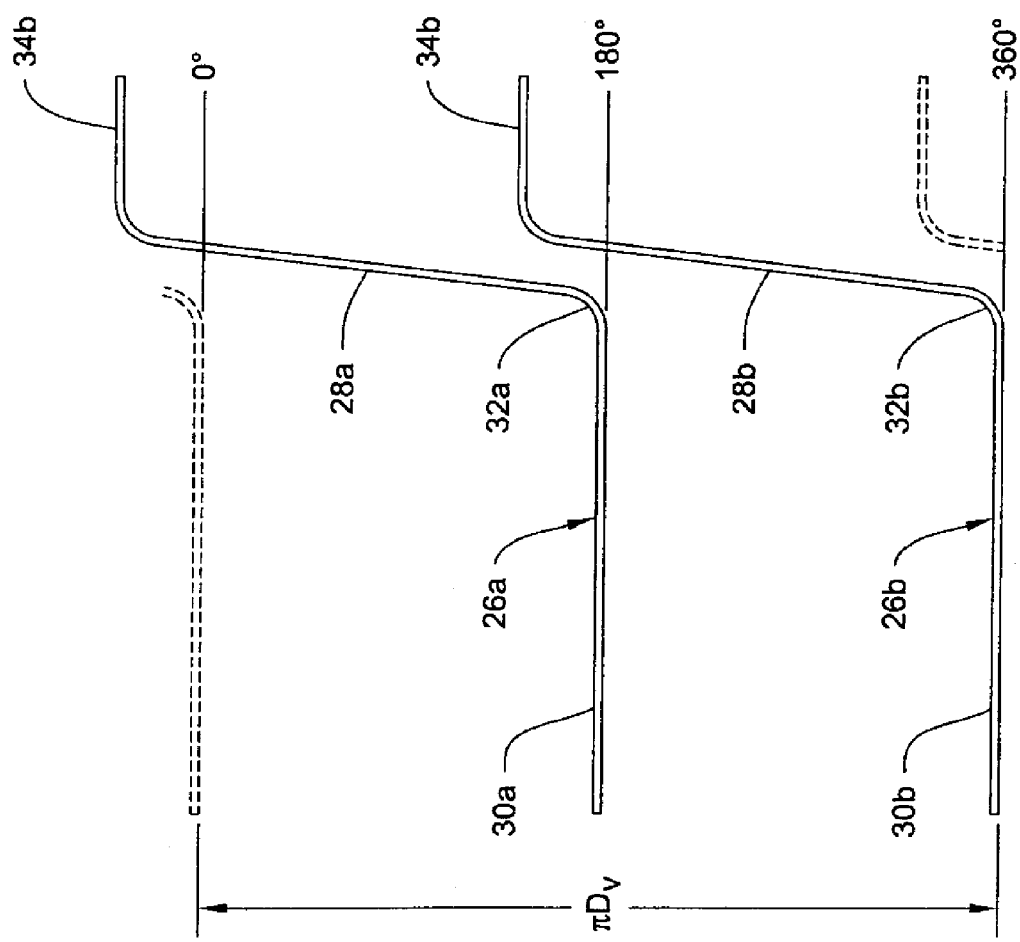
FIG. 3 is a flattened view of an example frame member.

Each of the one or more frame members 26a/b can each be configured to include a mouth defining portion, indicated by reference numbers 28a and 28b, and a shaft engaging portion, indicated by reference numbers 30a and 30b and best seen in FIG. 3. The mouth defining portions 28a/b may be arranged to define an opening or mouth 29 of filter 18. In some embodiments, mouth defining portions 28a/b form a portion of a generally circular filter mouth 29. For example, the two mouth defining portions 28a/b shown in FIG. 2 each span about 180° or are each roughly a semi-circular portion of a circular filter mouth 29. It can be appreciated that the shape of filter mouth 29 can vary without departing from the spirit of the invention. For example, filter mouth 29 may be oval, irregular, polygonal, or any other suitable shape. Moreover, the relative proportion of filter mouth 29 that each mouth defining portion 28a/b spans can also vary. For example each mouth defining portion 28a/b may span an equal proportion or each may span differing proportions.

Mouth defining portions 28a/b may be skewed or angled in the proximal or distal direction relative to the longitudinal axis of shaft 16. For example, mouth defining portions 28a/b may each include a proximal end 32a/b and a distal end 34a/b, and portions 28a/b may be skewed so that distal ends 34a/b are positioned distally along the longitudinal axis of shaft 16 relative to proximal ends 32a/b. This structural feature may result in a number of desirable features as described below. In some embodiments, distal ends 34a/b may include a slight curve or bend, which may decrease or otherwise blunt any sharpness that may be associated with distal ends 34a/b. Alternatively, distal ends 34a/b may include other modifications such as a solder or weld ball, a radiused or rounded end, and the like.

Shaft engaging portions 30a/b generally are the regions of frame assembly 20 where frame members 26a/b are coupled to shaft 16, for example by coupling 24. In general, shaft engaging portions 30a/b can be disposed adjacent shaft 16 so as to at least partially secure filter 18 to shaft 16. The exact attachment means can vary and is not necessarily limited to coupling 24. For example, shaft engaging portions 30a/b may be coupled to shaft by a mechanical bond such as a crimp, by adhesives, by thermal bond such as a weld, and the like.

As suggested above, the above features of device 10 may enhance the apposition of the walls of vessel 12 and/or the compliance to the vessel walls. It can be appreciated that the greater the wall apposition achieved by filter 18, the less likely it is that embolic debris will be able float past filter 18 at locations where filter 18 is spaced from the vessel wall. In at least some embodiments, the inclusion of a plurality frame members 26a/b allows frame assembly 20 to be more compliant to the vessel wall. More particularly, because mouth defining portions 28a/b of frame members 26a/b each define a portion of filter mouth 29 (e.g., each defining about 180° of a circular filter mouth 29), irregularities in the shape of the vessel wall can be "absorbed" by one frame member without having a major effect on the shape of the other. For example, a blood vessel having an inward projecting stenosis adjacent filter 18 could cause one of the mouth defining portions (e.g., portion 28a) to be partially displaced by the irregular or non-circular cross-sectional shape at the stenosis. However, because the remainder of the vessel may have a different, generally circular cross-sectional shape, the other mouth defining portion (e.g., portion 28b) can remain essentially apposed, independently of portion 28a. Thus, the overall wall apposition realized by device 10 may be enhanced relative to other filter types. Additionally, it may be desirable to add additional frame members, which may add to this feature.

In some embodiments, frame assembly 20 (including the individual components thereof) can be made of any suitable materials including metals, metal alloys, polymers, or the like, or combinations or mixtures thereof. Some examples of suitable metals and metal alloys include stainless steel, such as 304v stainless steel; nickel-titanium alloy, such as nitinol, nickel-chromium alloy, nickel-chromium-iron alloy, cobalt alloy, or the like; or other suitable material. The word nitinol was coined by a group of researchers at the United States Naval Ordinance Laboratory (NOL) who were the first to observe the shape memory behavior of this material. The word nitinol is an acronym including the chemical symbol for nickel (Ni), the chemical symbol for titanium (Ti), and an acronym identifying the Naval Ordinance Laboratory (NOL).

Additionally, frame assembly 20 can be configured from a number of structurally different members. For example, frame assembly 20 can be manufactured from wires, ribbons, tubes, and the like. These structures may have a generally round cross-sectional area, be flattened, be irregular in shape, etc. The used of wires or other "pre-assembled" structures may also help to decrease manufacturing cost by obviating the need to laser cut or otherwise process components of frame assembly 20.

Shaft 16 may also be comprised of materials similar to those listed above. In at least some embodiments shaft 16 can be a guidewire. It can be appreciated, however, that shaft 16 could also be essentially any medical device. For example, shaft 16 may comprise a catheter (e.g., therapeutic, diagnostic, or guide catheter), a tubular filter cartridge configured to be slidable over a guidewire or catheter, an endoscopic device, a laproscopic device, or any other suitable device.

Figure 4:
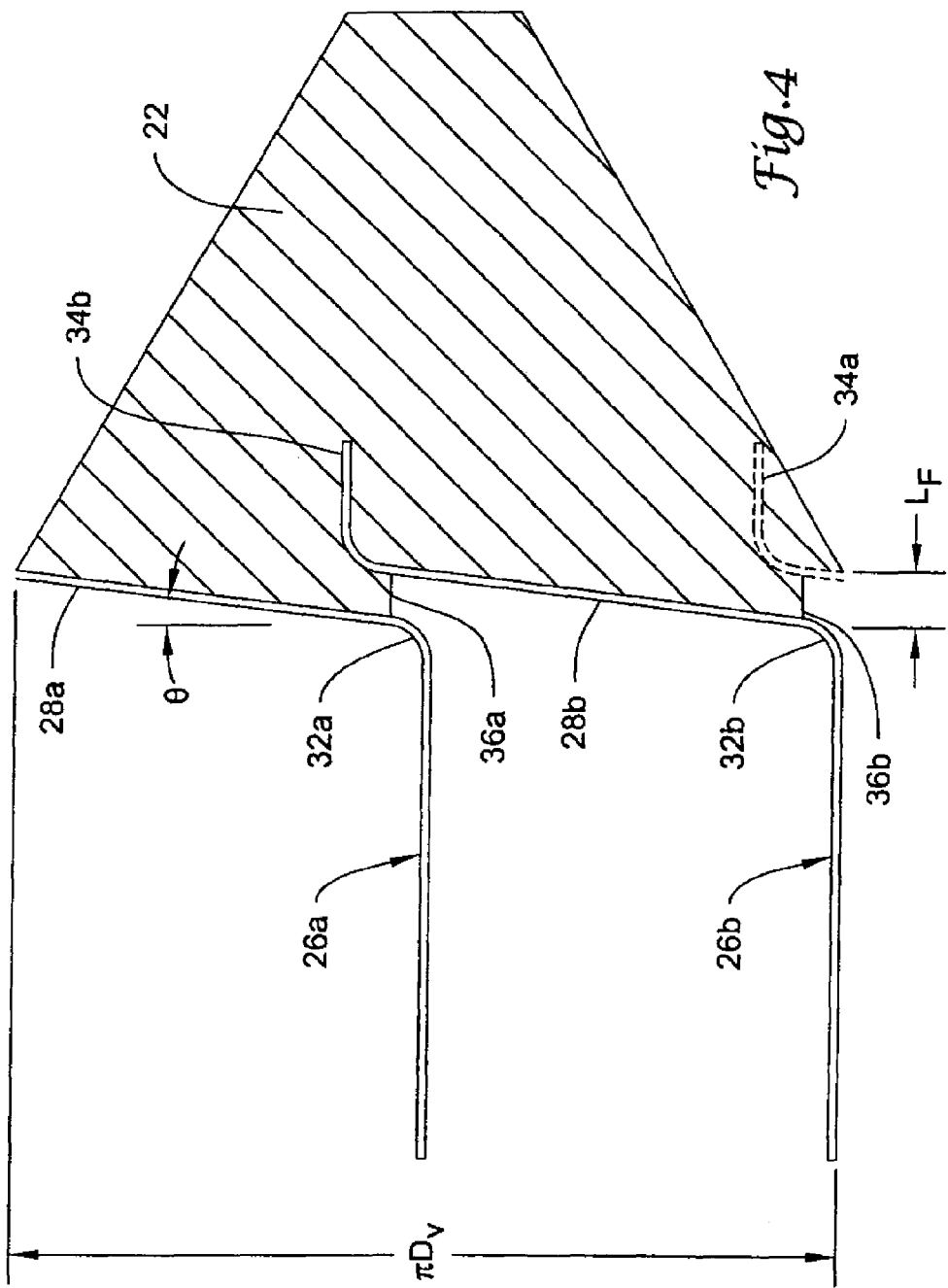
FIG. 4 is a plan view of an example frame member having a filter material coupled thereto.

The construction of device 10 may include steps generally illustrated in FIGS. 3 and 4. For example, FIG. 3 depicts a flat view of an example set of frame members 26a/b. Frame members 26a/b can be adapted and configured for the manufacture of filter 18 having the desired dimensions for the appropriate invention. For example, the lengths of members 26a/b can be varied relative to the circumference of the target site in a blood vessel ($\pi D_v$, where $D_v$ is the diameter of the blood vessel adjacent the target site) so that the size of filter mouth 29 approximates the circumference or size along the inside of the vessel wall. This feature allows filter 18 to have improved 360° apposition to the inside wall of the vessel.

Frame members 26a/b can be disposed over a mandrel (not shown) to bend them into the appropriate shape. For example, shaft defining portions 30a/b can be bent into a configuration appropriate for attaching them to shaft 16. Additionally, in at least some embodiments frame members 26a/b can be bent adjacent filter mouth defining portions 28a/b so that these regions are generally semi-circular. It can be appreciated that the invention should not be limited to only this particular shape and, in general, filter mouth defining portions 28a/b are configured to occupy as much of vessel circumference as desired. For example, the cross-sectional shape of the target site in the vessel may be slightly oval in shape or otherwise differ from being circular. Accordingly, the shape of mouth defining portions 28a/b can be varied to approximate these shapes and, thus, better achieve 360° wall apposition. As stated above, the relative proportions that each of the filter mouth defining portions 28a/b span can also vary.

At some point in the manufacturing process it may be desirable to couple or attach filter material 22 to frame assembly 20. For example, filter material 22 can be coupled to frame assembly 20 at mouth defining portions 28a/b as shown in FIG. 4. A number of different attachment mechanisms may be used to couple mouth defining portions 28a/b and filter material 22. Some suitable attachment mechanism may include adhesive bonding, thermal bonding, and the like.

As stated above, mouth defining portions 28a/b may be skewed or angled relative to the longitudinal axis of shaft 16. This skew angle $\theta$ can be seen in the flat view of FIG. 4 as a mouth defining portions 28a/b being slanted or angled. Skew angle $\theta$ of mouth defining portions 28a/b can be equal to each other as shown or may be different. The inclusion of skew angle $\theta$ can give filter 18 a number of desirable features. For example, if proximal ends 32a/b of mouth defining portions 28a/b are aligned, a vessel footprint length $L_f$ is defined that is proportional to angle θ. The footprint length $L_f$ is understood to be the length of filter 18 that can be in direct contact with the inside wall of the vessel. It can be appreciated that in at least some embodiments, regions of filter 18 that are distal of $L_f$ may be conical in shape and, thus, taper away from the vessel wall.

Because of skew angle θ, frame members 26a/b may be generally parallel to one another. According to these embodiments, one or more relatively short, bridging regions 36a/b of filter material 22 may be disposed between frame members 26a/b. It can be appreciated that the length of bridging regions 36a/b are about equal to each other and to footprint length $L_f$. In some other embodiments, the skew angle θ of each frame member 26a/b may be different and, thus, the lengths of bridging regions 36a/b may have different lengths. Bridging regions 36a/b can also prevent gaps from being present between frame members 26a/b, which can maintain the integrity of the vessel wall apposition.

As stated above, footprint length $L_f$ and skew angle θ are generally proportional to one another. More particularly, as angle θ becomes larger, footprint length $L_f$ becomes longer. Thus, a number of variations of angle θ and footprint length $L_f$ can be utilized in different embodiments of the invention. For example, it may be desirable due to the physiology or anatomy of the treatment site, for footprint length $L_f$ of filter 18 to be relatively short. According to this embodiment, manufacturing of filter 18 can include filter members 26a/b being skewed a relatively small skew angle θ.

Footprint length $L_f$ can also be related to the size the landing zone of the filter. The footprint length $L_f$ is understood to be the longitudinal length of filter 18 that is designed to be in contact with the vessel wall when filter 18 is deployed in the vessel. Landing zone is generally understood to be the overall longitudinal length of the filter. Thus, in embodiments where the footprint length $L_f$ is decreased, the landing zone can also be decreased. Having a short landing zone can advantageously permit filter 18 to be used at intravascular locations that are relatively short and would otherwise be inaccessible to traditional filters. For example, the length of a portion of the renal artery between the abdominal aorta and the kidney is relatively short. Diagnosis or other interventions at the junction of the renal artery and the kidney would not easily be accomplished by using conically shaped filter because the filter may extend into the kidney, possibly causing damage to the kidney. Thus, example embodiments of filter 18 having a generally short landing zone make this location more accessible for filtering. A number of additional intravascular locations may similarly benefit from example filters 18 having a shortened landing zone.

Figure 5:
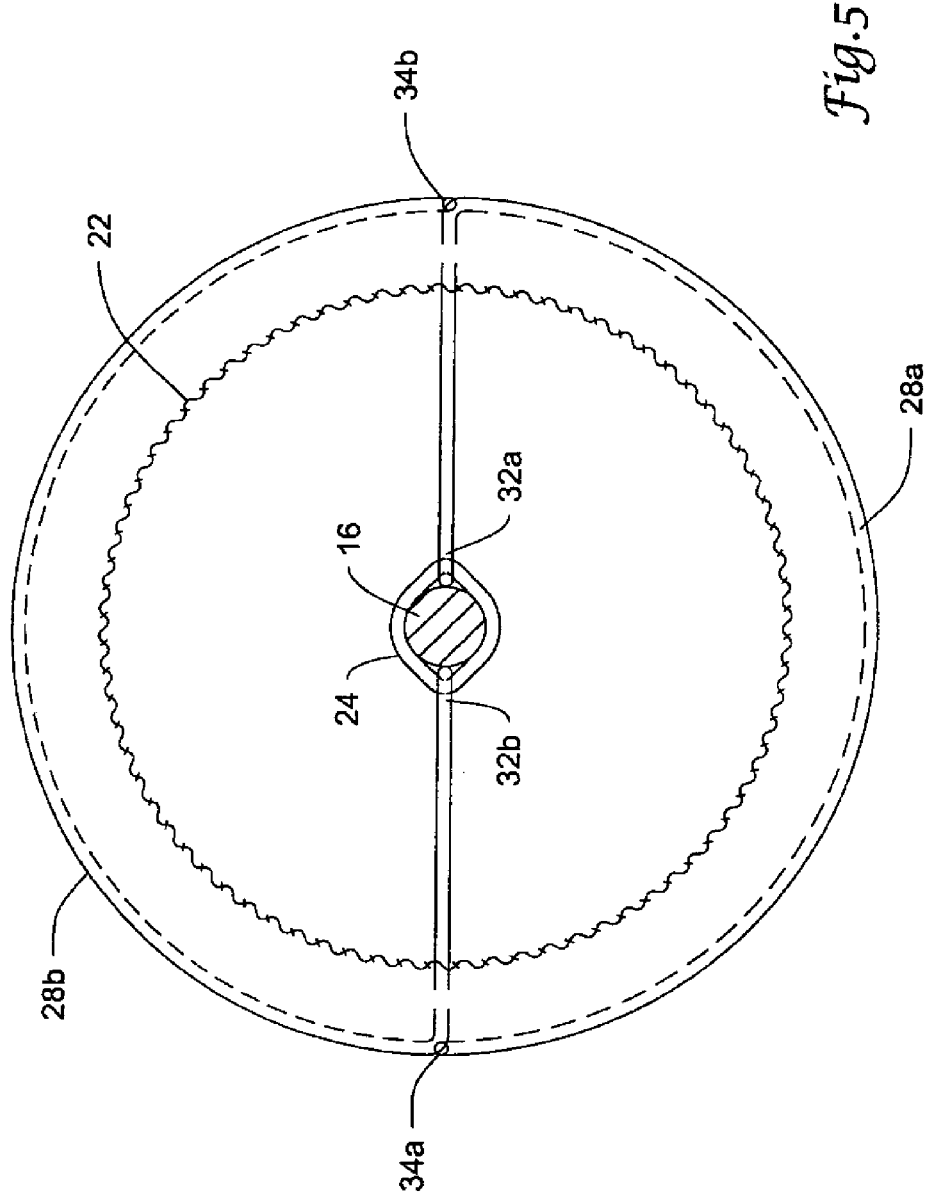
FIG. 5 is a cross-sectional view taken through line 5-5 in FIG. 2.
Figure 13:
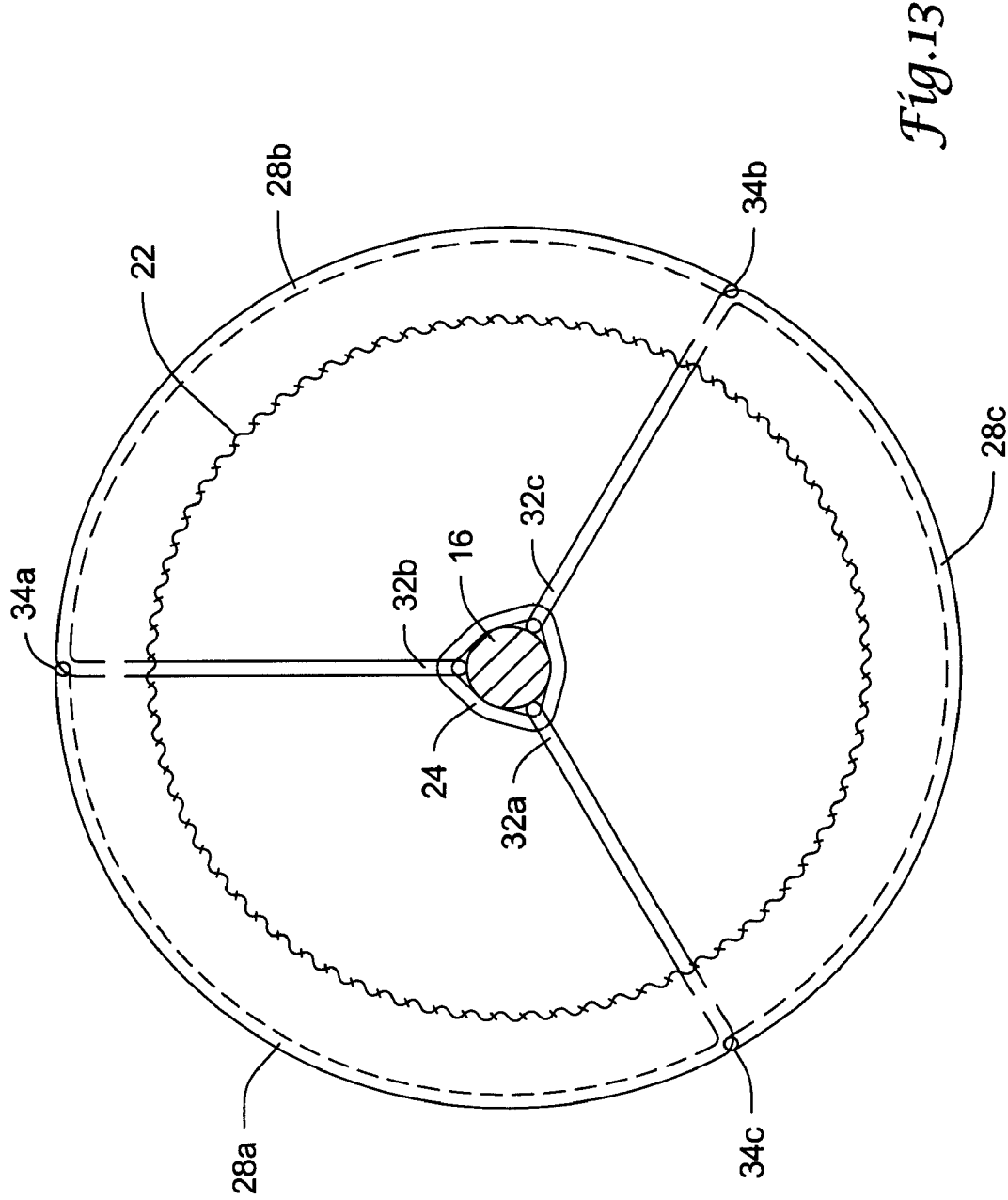
FIG. 13 is a cross-sectional view of another example embolic filter taken through a line analogous to line 5-5 in FIG. 2.

At the desired time in the manufacturing process, frame assembly 20 can be formed into the appropriate shape to define filter 18 (please see FIG. 2). A cross-sectional view taken through line 5-5 of FIG. 2 is shown in FIG. 5. From FIG. 5 it can be seen that each mouth defining portion 28a/b can be configured to span about 180°. As stated above, however, the relative proportion that each portion 28a/b can be varied as well as the number of mouth defining portions. For example, frame assembly 20 may include three proximal ends 32a/b/c, three distal ends 34a/b/c, and three mouth defining portions 28a/b/c, and each mouth defining portion 28a/b/c may span about 120° as illustrated in FIG. 13.

Figure 6:
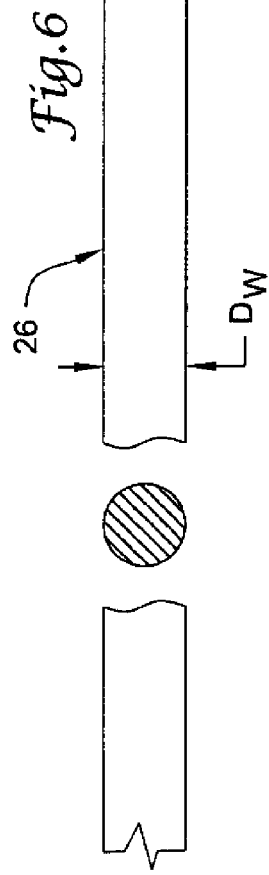
FIG. 6 is a plan view of a frame member.
Figure 7:
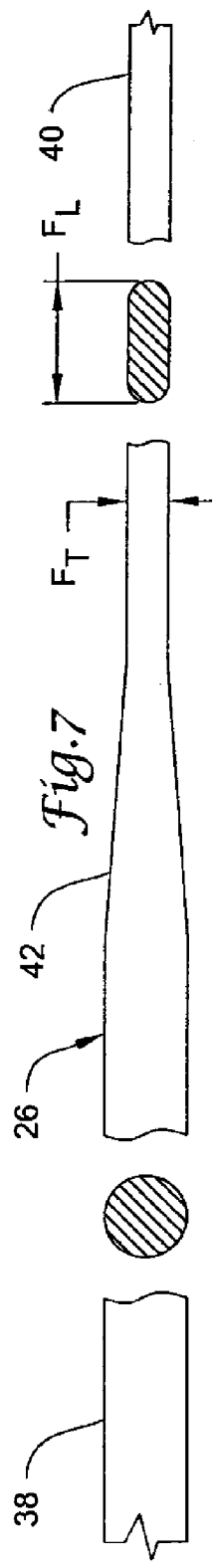
FIG. 7 is a plan view of a frame member that is partially flattened.

Frame members 26a/b can be shafts having a relatively constant outside diameter $D_w$ as shown in FIG. 6. According to this embodiment, a generic frame member 26 can be configured to have the desired shape, for example the shape depicted in FIG. 3. Alternatively, frame member 26 may be include a non-flattened portion 38 and a flattened portion 40 as shown in FIG. 7. Flattened portion 40 of frame member 26 may have a flattened thickness $F_T$ and a flattened cross-sectional length $F_L$, both of which may vary in alternative embodiments of the invention. A tapered portion 42 may be disposed between non-flatted portion 38 and flattened portion 40. It should be noted that in alternative embodiments, frame member 26 may comprise a generally flat or rectangular ribbon, which would include any desirable features of flattened portion 40.

In at least some embodiments, flattened portion 40 may be disposed adjacent the filter mouth defining regions 28a/b. Because of the attenuated $F_T$, disposing flattened portion 40 adjacent filter mouth defining regions 28a/b can reduce the crossing profile diameter of filter 18. This feature may be desirable, for example during interventions within small or sensitive blood vessels.

Figure 8:
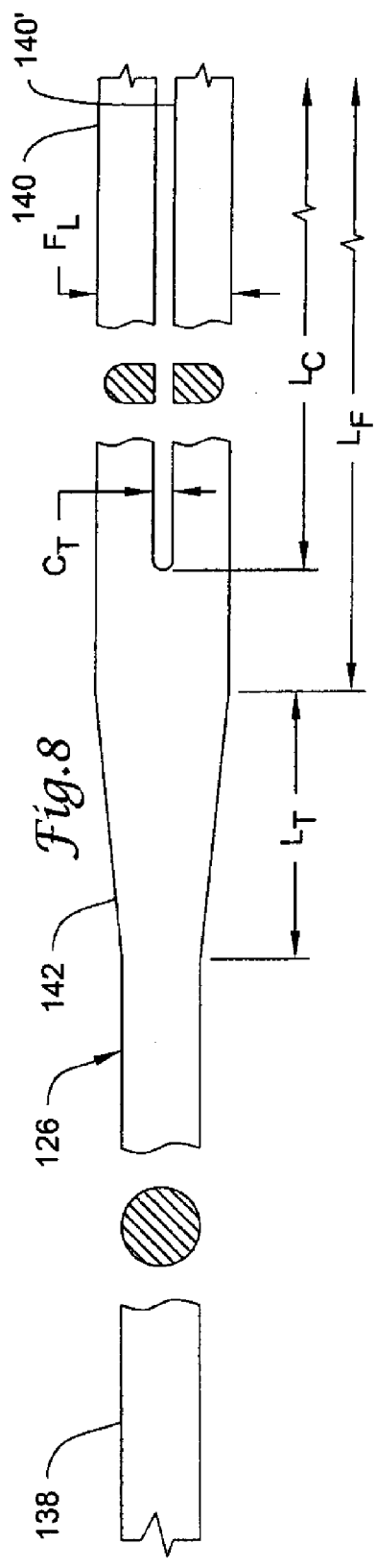
FIG. 8 is a plan view of a frame member that is partially flattened and split.

FIG. 8 illustrates an alternative example frame member 126. Frame member 126 is essentially the same as frame member 26 except that it flattened portion 140 is cut to define two flattened portions 140/140'. Frame member 126 may also include a tapered region 142. It can be appreciated that variations to the length of the taper LT (i.e., the length of frame member 126 adjacent taper 142), the length of flattened portion LF, thickness of the cut CT, and length of the cut region LC of frame member 126 are within the scope of the invention.

Figure 9:
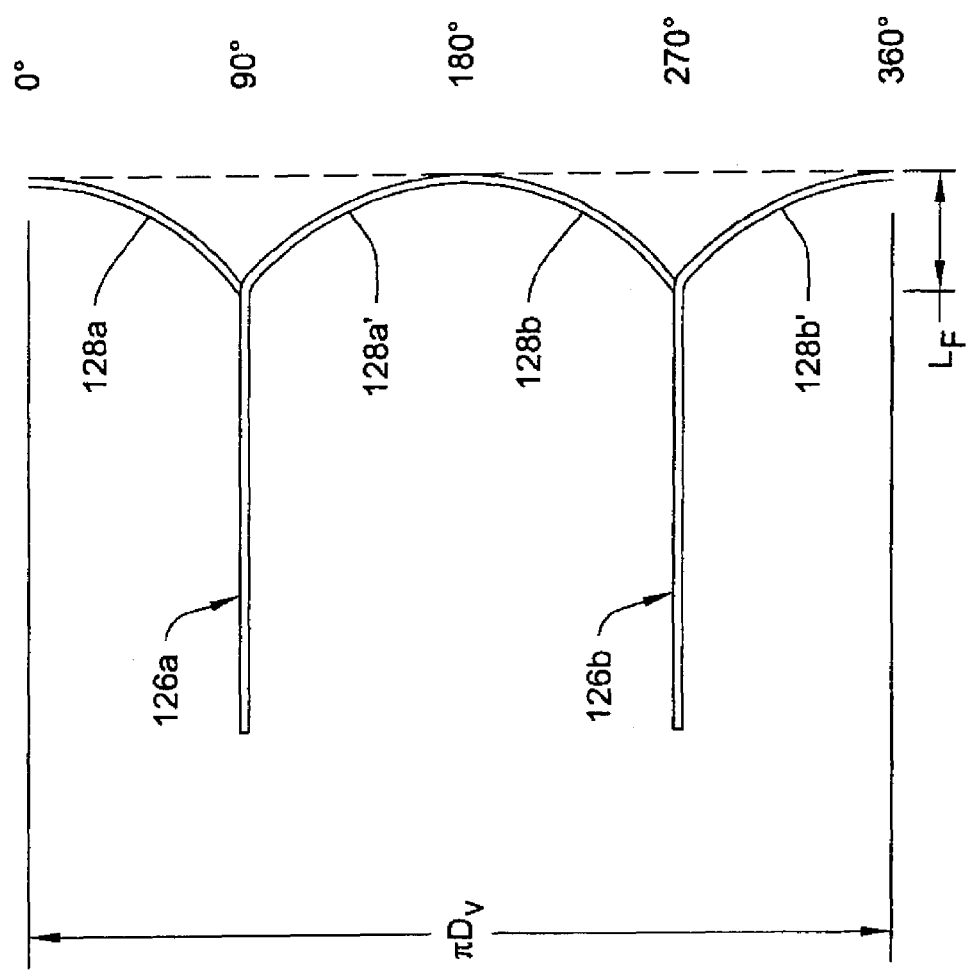
FIG. 9 is a flattened view of another example frame member.
Figure 10:
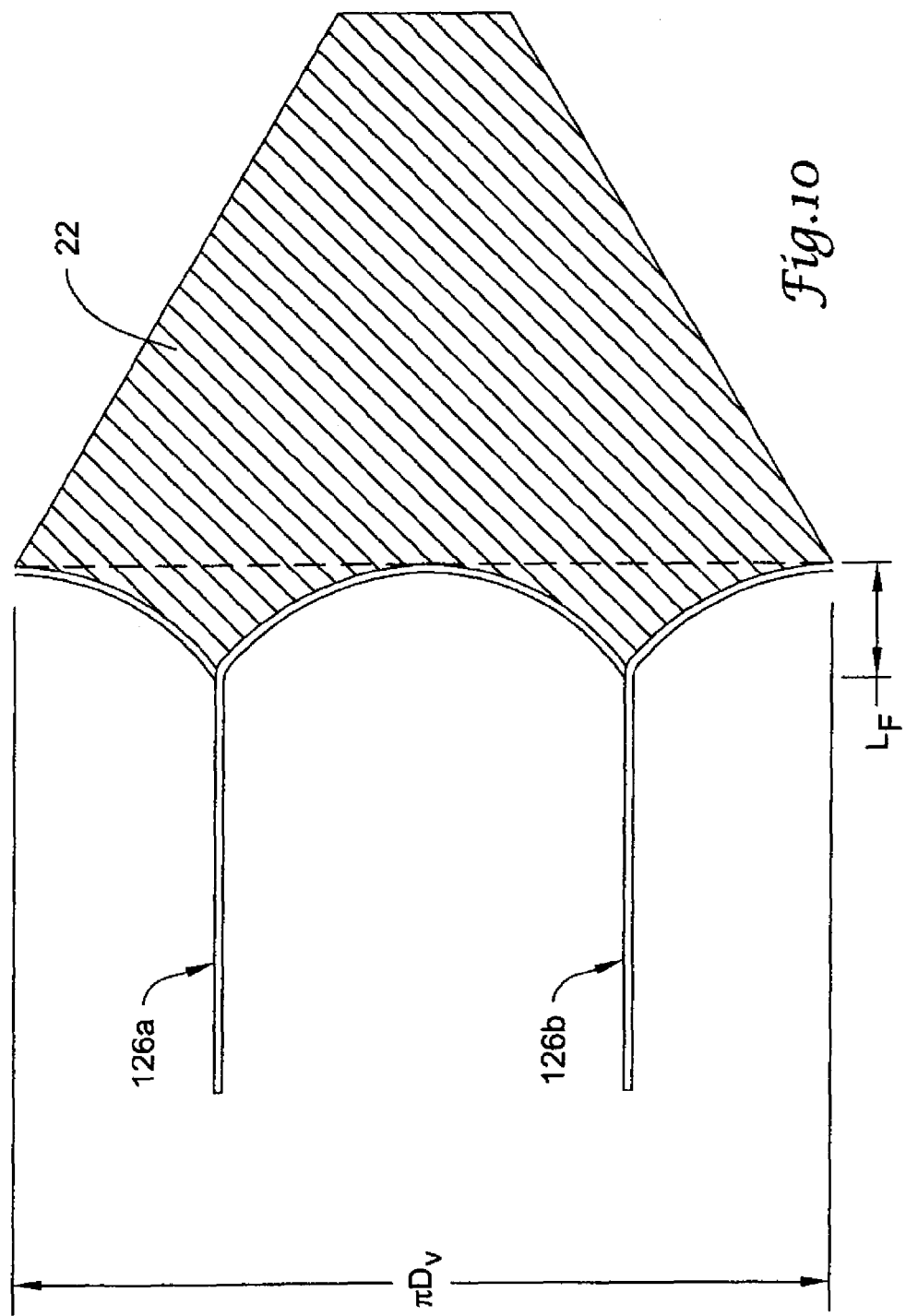
FIG. 10 is a plan view of another example frame member having a filter material coupled thereto.

One or more of frame members 126 may be used to manufacture an alternative example filter. For example, FIG. 9 illustrates a flattened view of frame members 126a/b configured in a fashion that is essentially analogous to the flattened view shown in FIG. 3. According to this embodiment, each frame member 126a/b includes a multi-leg filter mouth defining portion 128a/a' and 128/b/b'. It can be seen in FIG. 9 that the legs are at least partially curved. The amount of or sharpness of the curve can be altered to vary the footprint length $L_F$, similar to how skew angle θ can be varied in the above discussion. Similar to what is described above, filter material 22 can be coupled to frame members 126a/b as shown in FIG. 10.

Figure 11:
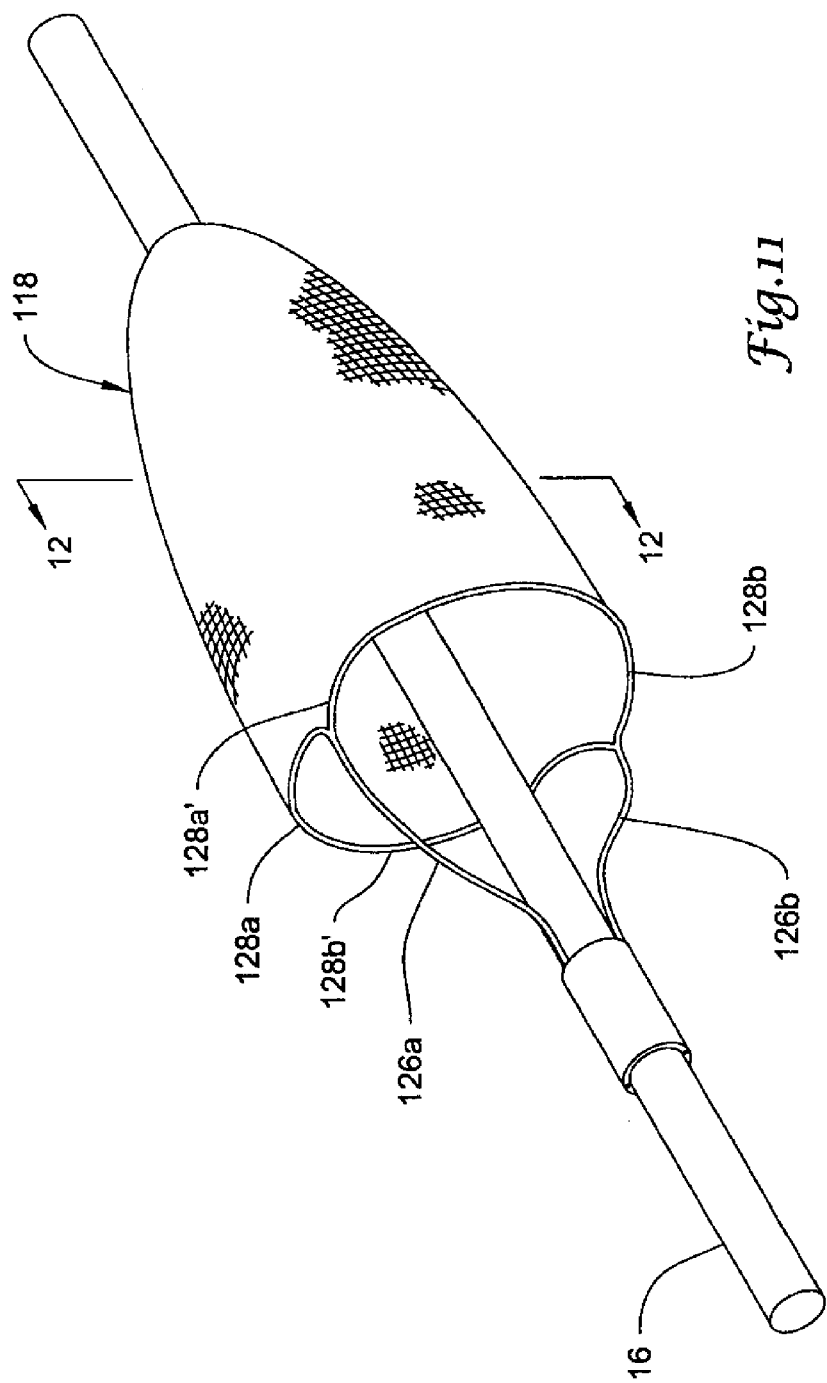
FIG. 11 is a perspective view of another example embolic protection device.
Figure 12:
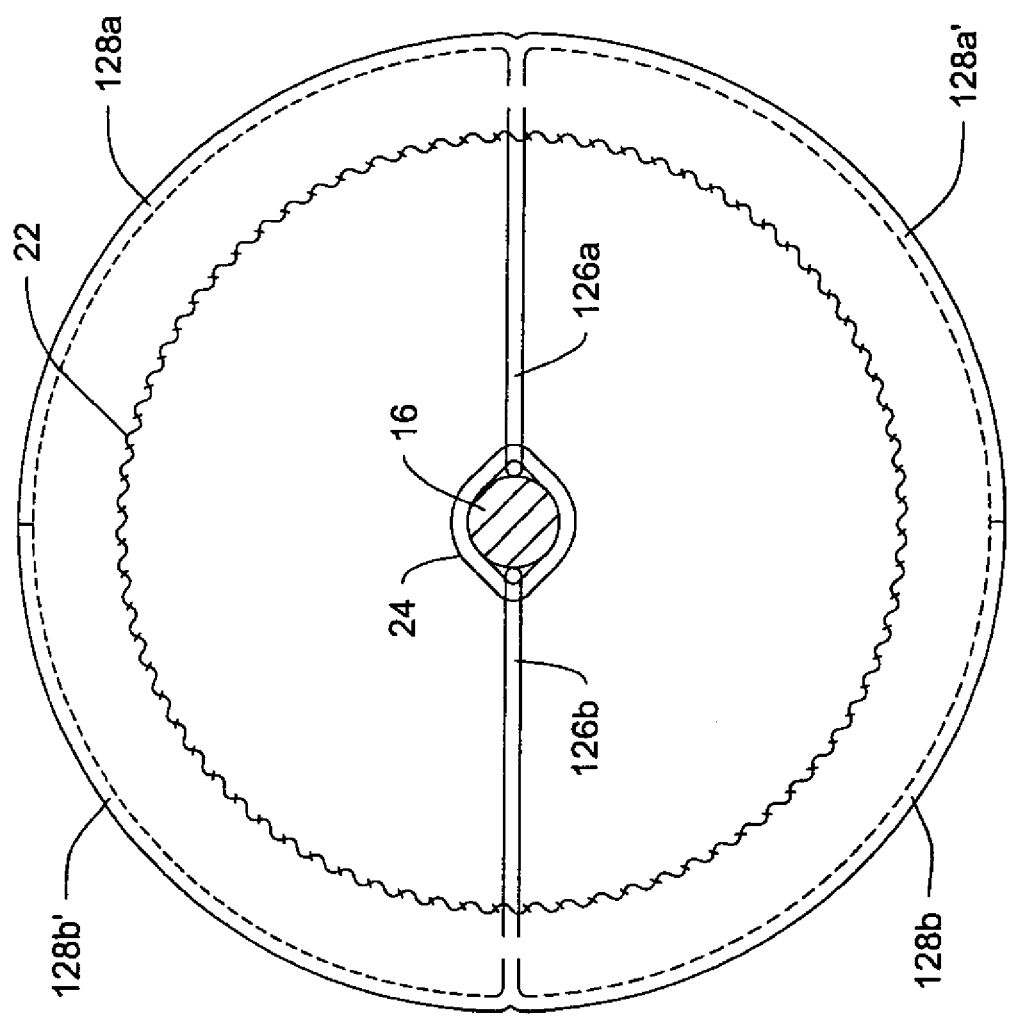
FIG. 12 is a cross-sectional view taken through line 12-12 in FIG. 11.

At the desired time in the manufacturing process, filter members 126a/b can be formed into the appropriate shape to define a filter 118 as illustrated in FIG. 11. The resultant filter 118 is essentially the same in form and function as filter 18 except that frame members 126a/b include multi-leg mouth defining portions 128a/a' and 128b/b' as described above. A cross-sectional view of filter 118 that is taken through line 12-12 is shown in FIG. 12.

It should be understood that this disclosure is, in many respects, only illustrative. Changes may be made in details, particularly in matters of shape, size, and arrangement of steps without exceeding the scope of the invention. The invention's scope is, of course, defined in the language in which the appended claims are expressed.

What is claimed is:

1. An embolic protection filter assembly, comprising:
   a first frame member comprising a first elongate member having a first end and a second end, the first elongate member including a first shaft-engaging portion proximate the first end and a first arcuate mouth portion proximate the second end;
   a second frame member comprising a second elongate member having a first end and a second end, the second elongate member including a second shaft-engaging portion proximate the first end and a second arcuate mouth portion proximate the second end;

wherein the first mouth portion and the second mouth portion collectively define a filter mouth;

a filter material coupled to the first and second frame members adjacent the first and second mouth portions; and an elongate shaft extending through the filter mouth, wherein the first end of each of the first and second elongate members is coupled to the elongate shaft, and the second end of each of the first and second elongate members is spaced radially away from the elongate shaft.

2. The assembly of claim 1, wherein the shaft comprises a guidewire.

3. The assembly of claim 1, wherein the shaft comprises a tube adapted and configured for being slidably disposed over an elongate wire.

4. The assembly of claim 1, wherein the filter mouth has a generally circular shape spanning 360 degrees.

5. The assembly of claim 4, wherein each of the first and second filter mouth portions includes one or more legs configured to span about 180 degrees of the filter mouth.

6. The assembly of claim 4, wherein the first and second filter mouth portions each span different proportions of the filter mouth.

7. The assembly of claim 4, further comprising a third frame member having a third shaft-engaging portion and a third arcuate mouth portion.

8. The assembly of claim 7, wherein each of first, second, and third arcuate mouth portions are configured to span about 120 degrees of the filter mouth.

9. The assembly of claim 7, wherein the first, second, and third filter mouth portions span different proportions of the filter mouth.

10. The assembly of claim 1, wherein the shaft has a longitudinal axis and wherein the first mouth portion is oriented perpendicularly to the longitudinal axis.

11. The assembly of claim 1, wherein the shaft has a longitudinal axis and wherein the first mouth portion is skewed at an angle relative to an axis pointed perpendicularly to the longitudinal axis.

12. The assembly of claim 11, wherein the angle is acute relative to the axis pointed perpendicularly to the longitudinal axis.

13. The assembly of claim 1, wherein the first and second mouth portions are connected by a bridging portion of the filter material disposed between the mouth portions.

14. The assembly of claim 1, wherein the first frame member includes a circular region having a generally circular cross-sectional shape and a flattened region having a generally oval cross-sectional shape.

15. The assembly of claim 14, wherein the flattened region is disposed adjacent the first filter mouth portion.

16. The assembly of claim 14, wherein the flattened portion is split to include a first leg and a second leg.

17. The assembly of claim 1, wherein the filter mouth collectively defined by the first mouth portion and the second mouth portion is a circular filter mouth.

18. The assembly of claim 17, wherein the elongate shaft extends concentrically through the circular filter mouth.

19. The assembly of claim 18, wherein the first and second mouth portions are each a semi-circular portion together forming the circular filter mouth.

* * * * *